United States Patent [19]
Triplett

[11] 4,448,763
[45] May 15, 1984

[54] ALTERATION OF GALLIUM BIODISTRIBUTION USING INDIUM COMPLEXES FOR ENHANCED EARLY IMAGING

[75] Inventor: John W. Triplett, Lexington, Ky.

[73] Assignee: The University of Kentucky Research Foundation, Lexington, Ky.

[21] Appl. No.: 205,423

[22] Filed: Nov. 10, 1980

[51] Int. Cl.$^3$ .................. A61K 43/00; A61K 49/00
[52] U.S. Cl. ........................................ 424/1.1; 424/9; 128/659
[58] Field of Search ............... 424/1, 9, 1.5; 128/659

[56] References Cited
PUBLICATIONS

*The Chemistry of Radiopharmaceuticals*, ed. Heindel et al., Masson Pub. USA, Inc., New York (1978) pp. 155–168.
J. W. Triplett et al., "Alteration of Gallium Distribution in the Rat Using periodically Related Elements", pp. 365–371 (1981).
*Semin Nucl Med*, 6: 331–334, 1976.
*Semin Nucl Med*, 8: 193–203, 205–218, 1978.
*J Nucl Med*, 21: 361–365, 421–425, 1980.
*J Nucl Med*, 17: 356–358, 1976.
*J Nucl Med*, 20: 248–251, 656, 1979.
*Radiology*, 131: 775–779, Jun. 1979.
*Radiology*, 130: 241–244, Jan. 1979.
*Nuclear Pharmacy Papers*, p. 68, date unknown at present.

*Primary Examiner*—Christine M. Nucker
*Attorney, Agent, or Firm*—Birch, Stewart, Kolasch & Birch

[57] ABSTRACT

Radiopharmaceutical compositions and methods for tumor tomography in mammals are disclosed, wherein radioactive gallium and non-radioactive indium are injected into said mammals whereby the affinity of said radioactive gallium for non-tumor tissues is decreased, resulting in enhanced imaging characteristics.

24 Claims, 13 Drawing Figures

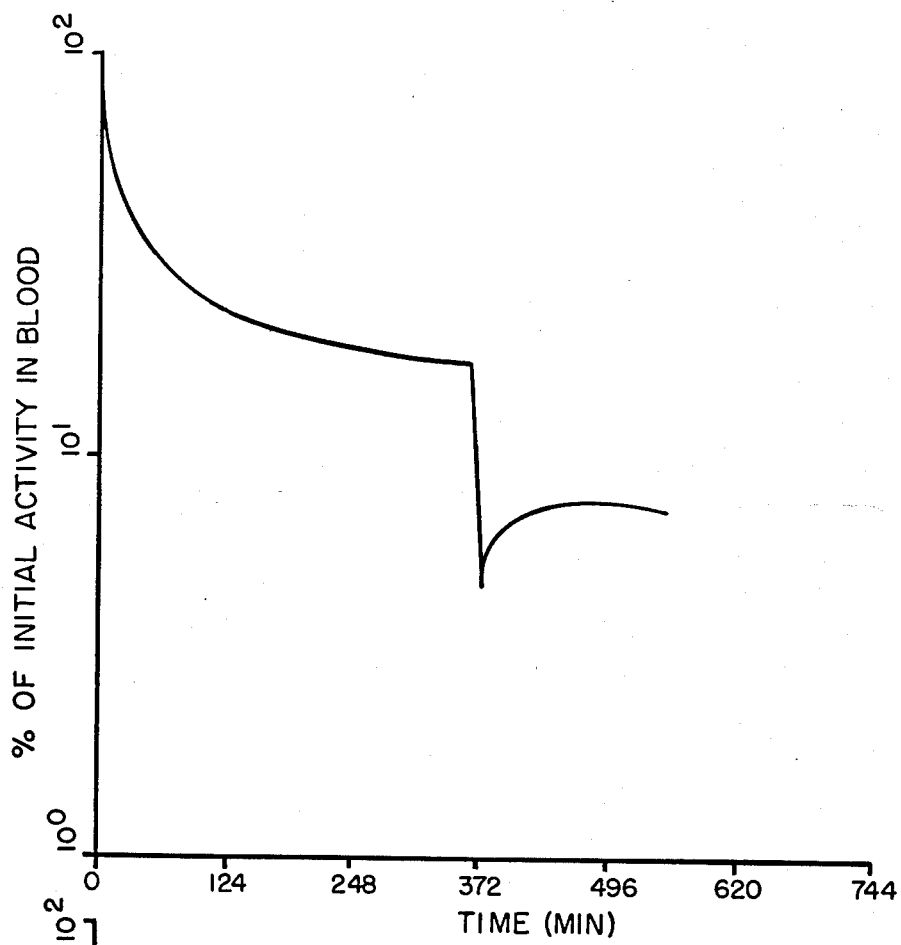
FIG. IC
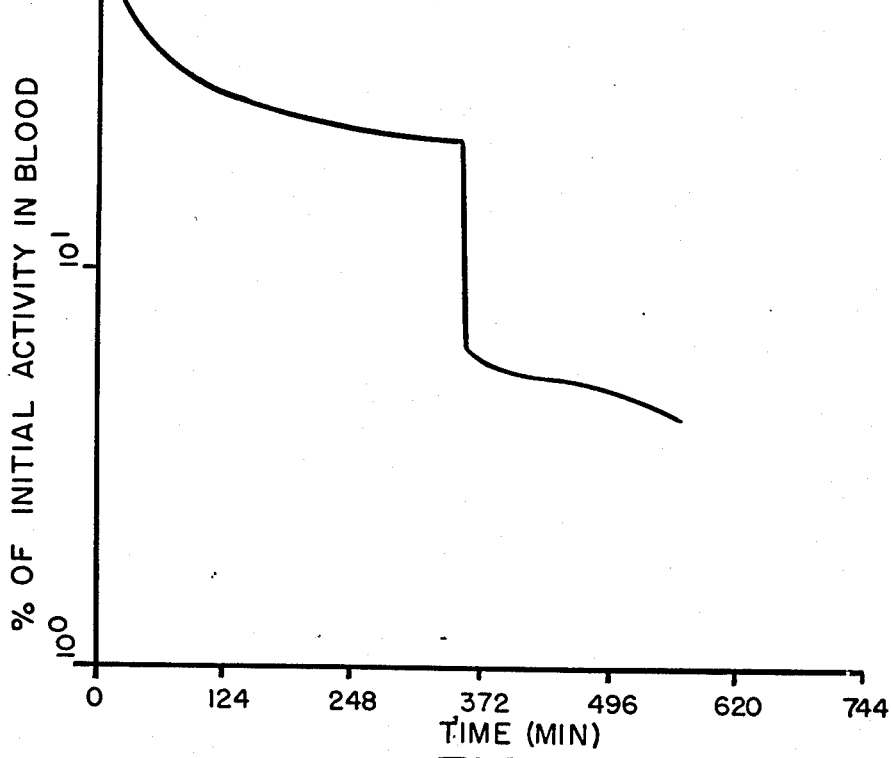
FIG. ID

ALTERATION OF GALLIUM BIODISTRIBUTION USING INDIUM COMPLEXES FOR ENHANCED EARLY IMAGING

BACKGROUND OF THE INVENTION

1. Field of the Invention

The present invention relates to a diagnostic nuclear medicine. More specifically, the present invention relates to tumor imaging utilizing radioactive gallium.

2. Description of the Prior Art

Gallium-67, as the carrier-free citrate, is used routinely in clinical medicine in the diagnosis, staging and monitoring of several neoplastic disease states (Semin Nucl Med 6: 331-334, 1976). Unfortunately, this agent is plagued with imaging problems which are related to plasma protein binding. Specifically, gallium has an affinity for blood and soft tissue proteins, and when given in very low doses, is extensively bound (J Pharmacol Exp Therapeut 168: 193-198, 1973). Gallium also has an affinity for tumors (Science 167:289-290, 1970; J Nucl Med 10: 103-105, 1969) and abscesses (J Nucl Med 21: 484-488, 1980). After intravenous administration, gallium activity in tumors is seen immediately and reaches a maximum within eighteen hours (Semin Nucl Med 8: 193-203, 1978). Biologic clearing of gallium from blood and soft tissue binding sites is a slow process, and results in the presence of image obscuring activity long after the ideal imaging time. Three major consequences of this binding phenomenon are: (a) it is necessary to delay imaging procedures for long periods of time (48-72 hours) to allow for the clearance of non-productive radioactivity; (b) the long waiting period allows the build-up of image obscuring activity in the intestinal tract due to secretion of gallium into the large bowel (J Nucl Med 14: 208-214, 1973); and (c) prolonged retention of large quantities of $^{67}$Ga in the body results in a relatively high radiation dose (J Nucl Med 12: 755-756, 1973).

Several reports have described methods or agents which attempt to enhance the process of imaging a tumor or abscess by shortening the biologic half life of carrier-free gallium-67 citrate. Generally, these fall into two categories: (a) agents which compete with radioactive gallium for blood and tissue binding sites, thus releasing the radioactive metal ion making it available for kidney elimination; or (b) complexing or chelating agents which compete with blood and tissue binding sites for free gallium, forming a complex which is rapidly cleared by the kidney.

The initial work took the first approach and used a group (IIB) metal complex (Scandium citrate) as a selective competitive binding agent (South Med J 66: 1339-1340, 1973; J Nucl Med 21: 361-365, 1980). Scandium, by occupying gallium binding sites on blood proteins, prevents the accumulation of gallium on these sites. Scandium appears to have little or no effect upon gallium binding in tumors. When used in animal studies, where gallium-67 and scandium citrates were injected simultaneously, extremely high tumor to blood and tumor to tissue ratios were obtained. Unfortunately, scandium produces a severe hemolytic anemia when administered to man (South Med J 66: 1339-1340, 1973; J Nucl Med 21: 361-365, 1980). The use of iron dextran in similar fashion to clear gallium from rabbits bearing induced abscesses resulted in the clearing of gallium with enhanced abscess uptake of gallium (J Nucl Med 17: 356-358, 1976). This ion, however, has no clinical application due to the large dose of iron required (J Nucl Med 21: 421-424, 1980). More recently, it has been shown that relatively large doses of non-radioactive gallium will decrease blood activity without significantly reducing tumor activity (J Nucl Med 20: 656, 1979; Invest Radiol 14: 482-492, 1979).

Several investigators have used the second approach, employing a chelating agent, desferoxamine, to reduce gallium blood activity (J Nucl Med 21: 421-425, 1980; J Nucl Med 20: 248-251, 1979; Radiology 131: 775-779, 1979; Radiology 130: 241-244, 1979). The resulting gallium desferoxamine complex is eliminated via the kidney at a rate greater than that observed for gallium alone. Unfortunately, this clearing agent must be administered 24 hours after the gallium injection in order to minimize loss of tumor activity.

SUMMARY OF THE INVENTION

It is, therefore, a primary object of the present invention to provide improved radiopharmaceutical compositions and methods for tumor imaging which overcome or reduce the above mentioned problems of the prior art.

Carrier-free solutions of gallium-67 citrate were administered to normal and tumored rats, and blood levels of radioactivity were monitored as a function of time. Metal complexes of aluminum, gallium, indium or thallium were administered at times varying from two to six hours following the injection of the radiopharmaceutical. In the cases of indium and gallium, the blood activity was observed to decrease very rapidly, and a generalized clearing of soft tissue activity was observed. Similar studies using imaging techniques, reveal that activity bound within tumors is obviously affected by the addition of moderate doses of carrier gallium. When indium citrate was administered two hours after the radiopharmaceutical the tumor activity increased significantly. When carrier-free gallium-67 was administered simultaneously with indium citrate, the biodistribution of gallium in rats bearing transplanted tumors (lymphoma and hepatoma) was found to be dramatically altered. Two hours after dosing, radioactivity is observed in the kidney, bladder, bone and tumor. Other areas and tissues were essentially void of activity. This rapid clearance of non-productive gallium from diffuse soft tissues, blood and organs such as liver, lung and spleen demonstrates the potential for use of the gallium-68 coupled with emission tomography.

Therefore, in accordance with the present invention, it has been discovered that intravenous injection of a non-radioactive indium complex simultaneously with, shortly before or shortly after, the intravenous injection of carrier free gallium-67($^{67}$Ga) or gallium-68($^{68}$Ga), alters the biodistribution of the radioactive gallium. More specifically, the indium complex occupies non-tumor gallium receptor sites, and, therefore, the gallium will not be retained on these receptor sites to thereby obscure the imaging process. In other words, the indium complex has a high affinity for non-tumor gallium receptor sites leaving the gallium free to be bound to the tumor gallium receptor sites.

It has been shown that indium complexes alter gallium-67 biodistribution in rats bearing transplanted tumors (lymphoma and hepatoma).

The indium and gallium complexes may be administered by injection, with intravenous injection being preferred. The gallium complexes must be administered in carrier-free form with doses in the range of about 0.25 to 500 ng being preferred. In humans, doses up to 3 mg may be employed. The indium complexes may be administered in doses of from about 0.1 to 0.7 mg with doses of from about 0.1 to 0.3 mg being preferred. In humans doses will be based on blood protein content, and may vary up to 50 mg.

All water-soluble forms of indium such as water-soluble salts may be used. These water soluble forms include water-soluble organic salts, water-soluble inorganic salts as well as various water-soluble complexes. Examples of water-soluble organic salts include indium citrate, indium lactate, indium tartrate, indium phytate, and indium phthallate. Examples of water-soluble inorganic salts are indium chloride, indium nitrate, indium sulfate, and indium bromide. Another useful form of indium is an indiumtransferrin complex.

All water-soluble forms of gallium such as water-soluble salts are also useful. Examples of water-soluble forms include water-soluble organic salts, water-soluble inorganic salts as well as various water-soluble complexes. Examples of water-soluble organic salts include gallium citrate, gallium lactate, gallium tartrate, gallium phytate and gallium phythallate. Examples of water-soluble inorganic salts include gallium chloride, gallium nitrate, gallium sulfate and gallium bromide. An example of another form of gallium is a complex of gallium and transferrin.

Radiopharmaceutical compositions may be prepared by dissolving the gallium and/or indium complex in any acceptable solvent such as water, normal saline, buffer normal to the pharmaceutical preparation, and mixtures thereof. Normal saline is preferred as a solvent.

It is preferred to administer the gallium and the indium simultaneously, however, the indium may be administered before or after the gallium, preferably within 2 hours before or after the gallium.

When gallium and indium are administered in accordance with the present invention the following advantages are realized: the time required for image obscuring blood and/or soft tissue radioactivity to clear the body, enabling one to obtain a clear image of the tumor, is reduced; the radiation dose to the patient is reduced by increasing the rate at which the radioactive gallium clears the body; and the short-lived position emitting gallium-68 isotope may be recorded by emission tomographic imaging equipment to thereby allow viewing of the tumor in three dimensions. The radioactive gallium may be measured by using external scintigraphic techniques (either photon or positron).

BRIEF DESCRIPTION OF THE DRAWINGS

Other objects and advantages of the present invention will become apparent from a study of the following non-limiting examples and drawings in which FIGS. 1A–1D are distribution profiles for carrier-free gallium-67 citrate:

FIG. 1A is a typical profile with no clearing agent added;

FIG. 1B is a typical profile observed when carrier gallium citrate (3.3 mg/Kg) is given 6 hours (360 min) after radiopharmaceutical dosing;

FIG. 1C is a typical profile observed when indium chloride (2.1 mg/Kg) is given 6 hours (360 min) after radiopharmaceutical dosing; and FIG. 1D is a typical profile observed when indium citrate (2.1 mg/Kg) is given 6 hours (360 min) after radiopharmaceutical dosing.

FIG. 3A shows the rats two hours after radiopharmaceutical dosing. At this point, the rat on the left received carrier gallium citrate (3.3 mg/Kg) and the rat on the right received indium citrate (2.1 mg/Kg).

FIG. 3B shows the rats three hours after radiopharmaceutical dosing and one hour after injection of the clearing agent.

FIG. 3C shows the rats five hours past radiopharmaceutical dosing and three hours after the clearing dose.

FIG. 4A is cumulative over the time period 0 to 10 min.

FIG. 4B is the time period from 10 to 20 min.

FIG. 4C is the time period from 20 to 30 min.

FIG. 4D represents the same time period taken one hour after the injection.

FIG. 4E represents the same time period taken two hours after the injection.

EXAMPLES

Figure 1A:
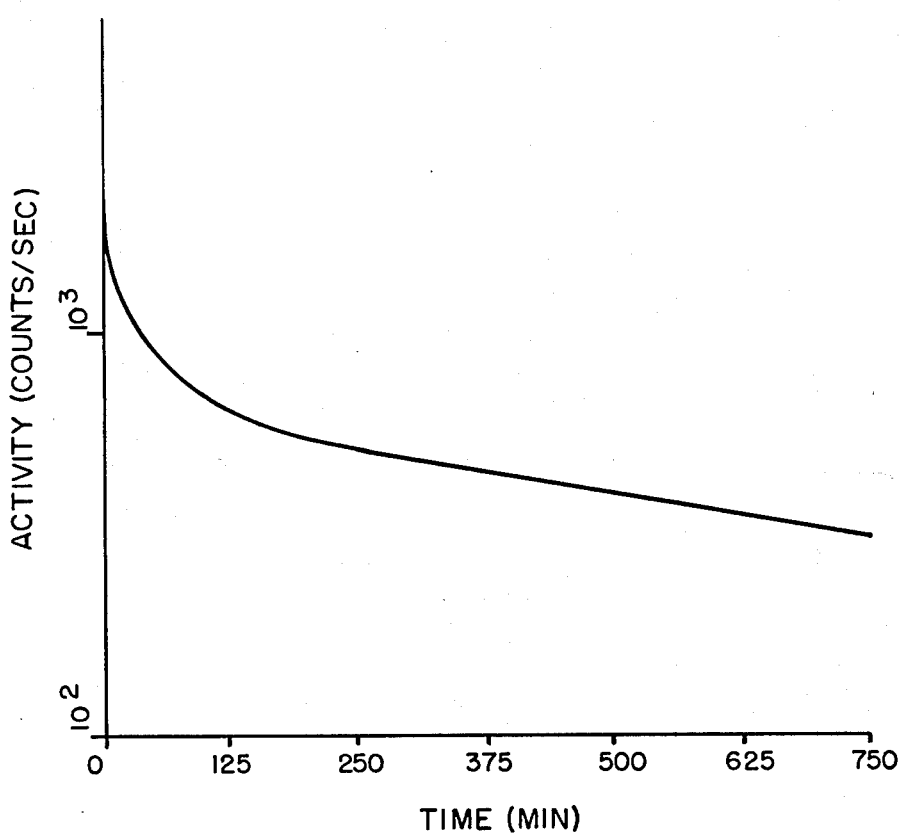

In this study, an external blood-loop technique (*Int J of Appl Radiat Isot* 29: 189–190, 1978) is used to monitor blood activity of the radiopharmaceutical as a function of time. Relative tissue concentrations are monitored by external imaging.

CHEMICALS AND RADIOPHARMACEUTICALS

All agents, both radioactive and non-radioactive, were used as purchased, without further purification. Gallium-67 citrate was obtained from Medi-Physics (Neoscan ®); thallium triacetate and indium chloride were obtained from Johnson-Mathey Chemicals Limited as the nonohydrate; and aluminum lactate was obtained from I.C.N. Pharmaceuticals.

Gallium citrate solutions were prepared by a method similar to that disclosed in *J Am Chem Soc* 72: 3822–3823, 1950. Gallium nitrate (375 mg) was dissolved in a minimum volume of boiling concentrated hydrochloric acid, citric acid solution (20% w/v, 2.5 ml) was added thereto, the resulting solution cooled to room temperature and neutralized with sodium hydroxide solution (final concentration: Ga 15 mg/ml-20 mg citrate/ml, pH 7.4). In a similar manner, indium citrate was prepared (final concentration: In 6.67 mg/ml-20 mg citrate/ml). Aqueous solutions of aluminum lactate (1.42 mg/ml) were obtained by solution in normal saline. All solutions were filtered (0.22μ millipore filter) prior to use.

ANIMAL PREPARATION AND RADIOPHARMACEUTICAL DOSING

For blood clearance studies, male Sprague Dawley rats weighing 250–300 grams were used. The animals were anesthetized by peritoneal injection of an aqueous solution of urethan (1 gm/Kg). The right carotid artery and left jugular vein were exposed and an external blood loop (PE-50 tubing; volume≃0.14 ml) was inserted between the vessels. Blood was diverted from the artery, through the loop, and back to the animal via the vein (*Int J of Appl Radiat Isot* 29: 189-190, 1978). The right external jugular vein was then exposed and cannulated as an injection site. The animal was placed in a lead cradle and the blood loop inserted into the shielded well of a sodium iodide.thallium crystal. The animal received an injection of carrier-free gallium citrate (100-120 μCi) via the jugular cannula. Blood activity within the loop was continuously monitored as a function of time using a Packard Model 9012 Multi-channel Analyzer/Multi-scaler system (Packard Instrument Co., Downersville, Ill.). Six hours post injection, the animal received a second injection containing one of the clearing agents (≃7.2 mmole/Kg). In subsequent experiments, clearing agents were administered two hours after or simultaneously with the radioactive dose.

Initial studies used non-tumored male Sprague Dawley rats weighing between 250 and 300 grams. Subsequent studies in tumored rats used male Buffalo rats bearing a 5123C hepatoma (The tumor line was initiated from donor animals donated by Drs. R. L. Hayes and B. Byrd of the Oak Ridge Associated Universities). In all imaging studies, the animals were anesthetized by intraperitoneal injection of urethane (1 gm/Kg), and the left external jugular vein cannulated as a dosing site. The animals were then positioned under the detection of the γ-camera (Union Carbide; CLEON 720 Large Field Gamma Camera coupled with a CLEON 110 Image Processor) and images were obtained periodically.

Following a single intravenous injection of carrier-free gallium-67 citrate in the normal Sprague Dawley rat, prepared as described, a blood activity-time curve similar to that shown in FIG. 1A is observed. The curve is characterized by a rapid distribution phase followed by a slower elimination phase. The rapid distribution process appears to be complete four to six hours after dosing and is in itself multiplastic. There is a very rapid component ($t_{\frac{1}{2}}=12$ seconds) which may be due to kidney elimination of the citrate complex. This process would become insignificant as gallium complexed with citrate is transferred to binding sites on blood proteins, thus becoming less available for kidney elimination.

Figure 1B:
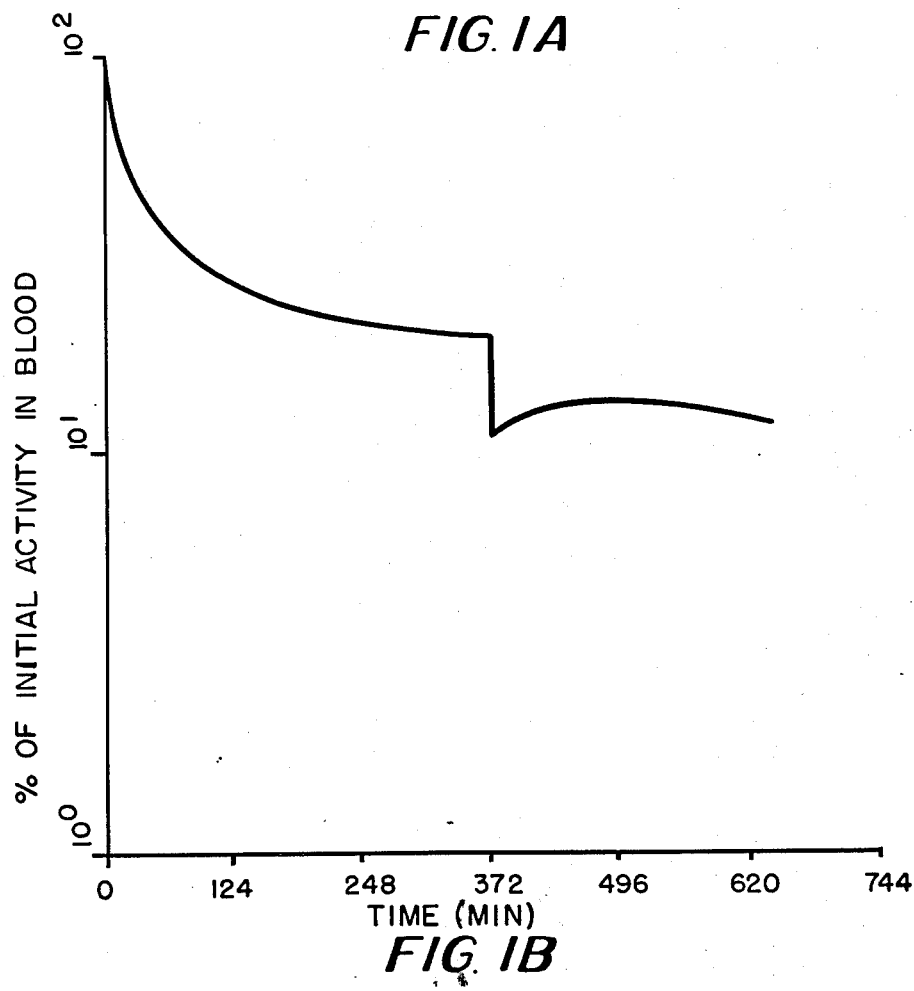

The effect of a relatively large dose of non-radioactive gallium (3.3 mg/Kg) given six hours after the initial injection is seen in FIG. 1B. There is a dramatic, rapid drop in blood activity (approximately 40% of the blood activity is removed). This is followed by a rise in blood activity, possibly due to release of $^{67}$Ga from less available gallium stores by an isotopic exchange process. The rise in blood activity peaks 1.5 to 2 hours after the second injection and subsequent gallium elimination parallels that observed when no clearing agent is used. When gallium is administered in this manner, the blood activity measured eight hours post radiopharmaceutical dosing, is approximately 25% less than that observed when no clearing agent is given.

In similar experiments, equimolar quantities of non-radioactive aluminum, indium, or thallium complexes were injected six hours after the carrier-free gallium dose. The results of these studies are summarized in Table 1.

TABLE 1

Relative ability of the group (IIIA) metals to clear $^{67}$Ga from blood six hours after injection of the radiopharmaceutical

| Non-radioactive Metals | % Decrease in Blood Activity | % Increase in Blood Activity | Net Decrease |
|---|---|---|---|
| Thallium | 0 | 0 | 0 |
| Aluminum | 9 | 3 | 6 |
| Gallium | 40 | 15 | 25 |
| Indium (Cl) | 85 | 25 | 60 |

There was no change in blood activity following a dose of 7.2 mmoles/Kg of thallium triacetate. Aluminum lactate caused a reduction of 9% in blood activity followed by a 3% rise in activity. The net reduction in blood activity was only 6%. Indium chloride proved to be the most potent of the clearing agents tested. As was the case with non-radioactive gallium, indium chloride (FIG. 1C) caused a rapid drop in blood activity (85%) followed by an increase which peaked 1.5 to 2 hours after the clearing dose was given. The net reduction in blood activity was 60%. When indium citrate was used in similar fashion, the blood curve was observed to fall 77% and there was no significant rise in blood activity (FIG. 1D). The distributional difference between indium chloride and indium citrate could be explained if citrate offered a weak, transient binding for that gallium which is displaced from the blood protein binding sites now occupied by indium. The gallium citrate complex thus formed must be rapidly cleared by the kidney. This is the same mechanism suggested above for the rapid drop in blood activity seen at early times. In the absence of citrate, gallium would seek alternate, non-vascular, binding sites (probably surface proteins in tissues) from which it would undergo a slower redistribution to blood sites vacated as indium undergoes distribution processes.

The two most successful clearing agents, gallium and indium citrate, were further investigated to determine if varying the length of time between radiopharmaceutical dosing and clearing agent dosing altered the results. Gallium (3.3 mg/Kg) cleared 78% of the blood activity when given at two hours after the radiopharmaceutical. This was followed by the characteristic rise in activity which resulted in a net clearance of 70%. Indium citrate reduced the blood activity by 78% and no subsequent rise in activity was observed.

Figure 2B:
FIG. 2 is a rectilinear scan of a normal Sprague Dawley rat before and after a clearing dose (3.3 mg/Kg) of non-radioactive gallium citrate was administered six hours post radiopharmaceutical dosing.
Figure 2A:

Preliminary imaging studies performed in non-tumored rats injected with one of the four clearing agents six hours post dosing, gave results which generally paralleled the blood studies. Injections of thallium or aluminum yielded no significant redistribution of the radioactivity. Injections of non-radioactive gallium or indium citrate shifted the radioactivity out of the blood/soft tissue regions and into the kidneys and the bladder (FIG. 2).

Clearing studies were performed on tumored rats using these agents in dosages suggested as optimal in both blood and preliminary imaging studies. Indium citrate was dosed at the level of 2.1 mg/Kg, and gallium citrate was dosed at 3 mg/Kg and 15 mg/Kg. When given six hours after the initial injection, the high dose of non-radioactive gallium resulted in obvious redistributions of radioactivity which would have obscured chest and abdominal images (i.e. liver, spleen, lung and intestine). However, tumor activity was observed to decrease. The lower dose of gallium generally has a less dramatic effect in that a great deal of activity remains in the abdomen, particularly in those organs with high reticuloendothelial (RE) activity (liver and spleen). Also, loss of activity from the tumor is much less. Indium is obviously the superior agent, reducing activity within the RE rich tissues while not depleting tumor activity. However, the effect is not dramatic enough to indicate clinical significance.

Figure 3A:
FIGS. 3A–3C are scans (Union Carbide Cleon model 720 large field gamma camera) of Buffalo rats bearing implanted 5123C hepatomas.
Figure 3B:
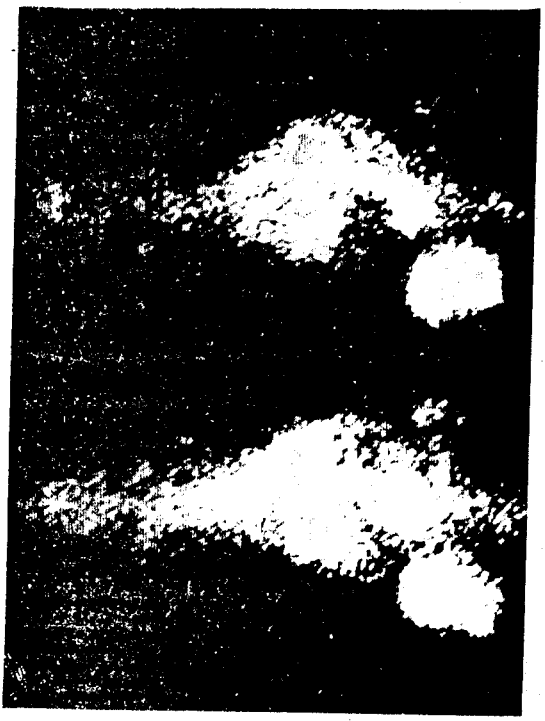
Figure 3C:
Figure 4C:
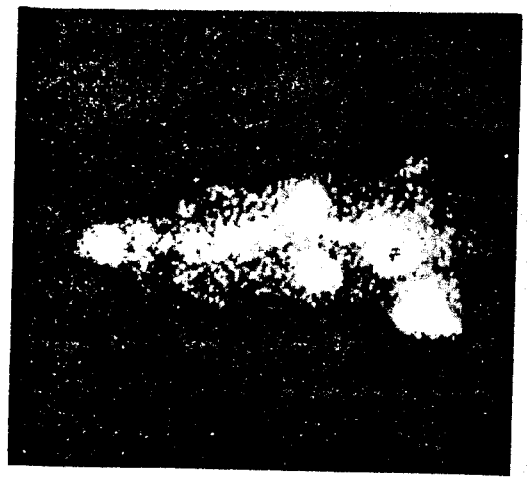
FIGS. 4A–4E are scans (Union Carbide Cleon model 720 large field gamma camera) of Buffalo rats, bearing Morris 5123C hepatoma is injected with a single solution containing carrier-free gallium-67 citrate and 2.1 mg/Kg indium citrate.
Figure 4B:
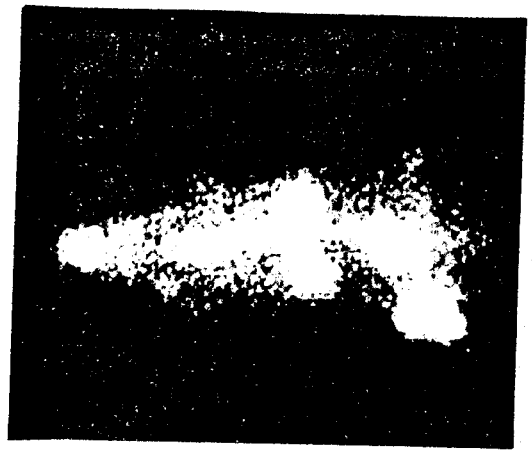
Figure 4A:
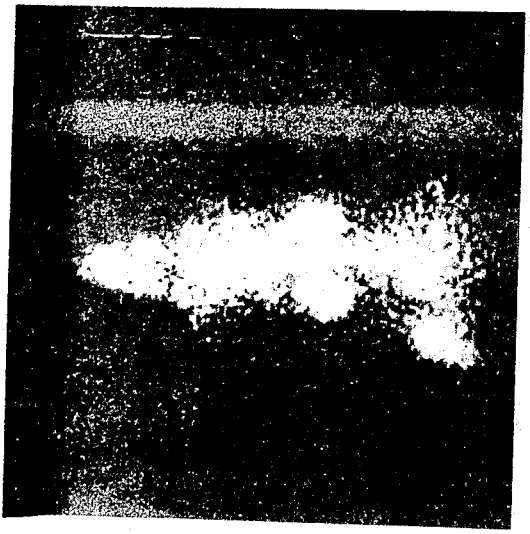
Figure 4E:
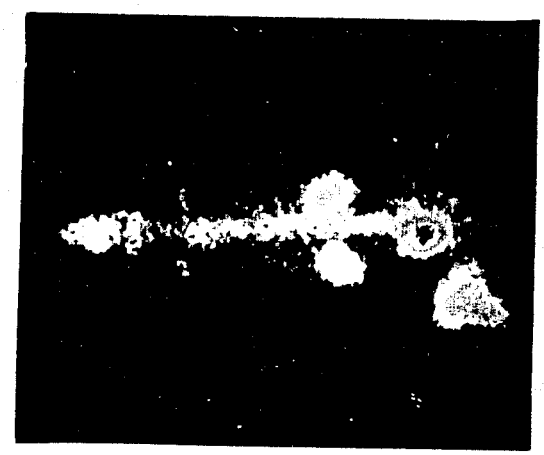
Figure 4D:

When the clearing agent was given two hours post radiopharmaceutical dosing, there were significant changes in gallium-67 distribution (FIG. 3). Gallium citrate (3 mg/Kg) causes some clearing in the upper abdomen and in regions of the lower abdomen. There was little loss of activity from the tumor region and the diagnostic potential of the image was improved. The results from use of indium citrate were somewhat more dramatic in that the activity is greatly diminished throughout the soft tissue regions. Activity in the liver-spleen-lung region is greatly reduced as it is in the lower abdomen. The most significant distributional change, however, is the obvious increase in tumor activity. This suggests that the mechanisms by which gallium localizes in tumor must differ from that directing its localization in other tissues and blood. Further, this suggests that indium, like scandium, may allow tumor localization of activity while preventing the accumulation of activity in blood and tissue when given simultaneously with the radiopharmaceutical. To test this hypothesis, indium citrate was given with gallium-67 citrate as a single solution. As shown in FIG. 4, the distributional pattern of gallium-67 is drastically altered. Twenty minutes after the mixed dose is given, there is little activity outside the kidneys, bladder, tumor and bone. After two hours, there is essentially no activity in the animal other than in the above mentioned regions.

Indium citrate, has the ability to successfully compete with gallium for blood and soft tissue binding sites, yet it does not compete for gallium binding sites in tumor. This is a property shared with scandium and iron. It is potentially a clinically significant finding in that gallium-67 citrate, under the distributional influence of this type agent could be useful for general metastatic searches. No longer would the liver-spleen region, a common metastatic site, be obscured by activity taken up by the RE system. Further, because of the reduced time between dosing and imaging, significant abdominal secretion does not occur, thus the gut area is free of activity.

Unlike scandium, indium is not known to rupture red blood cells. Toxicity studies following single doses of indium citrate indicate that the doses used in this study for clearing gallium are in the toxic range (*Proc Soc Exp Biol Med* 29: 1188–1193, 1931; *Cancer Chemother Rep* Part 1 59: 599–610 1975; *J Indust Hyg Tox* 24; 243–254, 1942). However, preliminary blood studies in normal rats suggest that clearing dose of indium citrate can be reduced by as much as an order of magnitude without loss of clearing potential. Indium doses in this range were not reported to be toxic.

The use of indium citrate simultaneously with the radiopharmaceutical could shorten the dose-to-image waiting period from day to minutes, making possible the use of the shorter lived isotope gallium-68 ($t_{\frac{1}{2}} = 68$ minutes) for tumor imaging. This isotope, while biologically identical to gallium-67, has the added advantage of positron emission, introducing the potential for emission tomography and all the inherent advantages of three dimensional imaging.

The invention being thus described, it will be obvious that the same way be varied in many ways. Such variations are not to be regarded as a departure from the spirit and scope of the invention, and all such modifications as would be obvious to one skilled in the art are intended to be included within the scope of the following claims.

What is claimed is:

1. A radiopharmaceutical composition, comprising: radioactive gallium, non-radioactive indium and a pharmaceutically acceptable carrier or diluent.

2. A radiopharmaceutical composition according to claim 1, wherein said radioactive gallium is gallium 67 or gallium 68.

3. A radiopharmaceutical composition according to claim 1, in the form of an injectable solution.

4. A radiopharmaceutical composition according to claim 3, wherein said gallium and indium are present in the form of water-soluble salts or complexes.

5. A radiopharmaceutical composition according to claim 4, wherein the concentration of said indium in said injectable solution is between 0.3 mg/ml and 2.1 mg/ml.

6. A radiopharmaceutical composition according to claim 5, wherein the said gallium in said injectable solution is in carrier-free form.

7. A radiopharmaceutical diagnostic kit, comprising: an effective tumor imaging amount of water-soluble radioactive gallium; and an effective tumor imaging improving amount of water-soluble non-radioactive indium.

8. A method for detecting tumors in mammals comprising: administering to said mammals an effective tumor imaging amount of radioactive gallium and an effective tumor imaging improving amount of non-radioactive indium and measuring the biodistribution of said radioactive gallium using external scintigraphic techniques.

9. A method according to claim 8, wherein said gallium is administered by injection.

10. A method according to claim 9, wherein said indium is injected in an amount of between 0.1 mg/Kg and 2.1 mg/Kg.

11. A method according to claim 9, wherein said gallium is injected in carrier-free quantities.

12. A radiopharmaceutical composition according to claim 1, wherein said composition includes a water-soluble organic salt of radioactive gallium.

13. A radiopharmaceutical composition according to claim 1, wherein said composition includes a water-soluble organic salt of non-radioactive indium.

14. A radiopharmaceutical composition according to claim 1, wherein said composition includes radioactive gallium citrate.

15. A radiopharmaceutical composition according to claim 1, wherein said composition includes non-radioactive indium citrate.

16. A pharmaceutical composition according to claim 1, wherein said composition includes a water-soluble inorganic salt of radioactive gallium.

17. A pharmaceutical composition according to claim 1, wherein said composition includes a water-soluble inorganic salt of non-radioactive indium.

18. A radiopharmaceutical composition according to claim 1, wherein said composition includes an organic salt of radioactive gallium selected from the group consisting of gallium citrate, gallium lactate, gallium tartrate, gallium phytate and gallium phythallate.

19. A radiopharmaceutical composition according to claim 1, wherein said composition includes an inorganic salt of radioactive gallium selected from the group consisting of gallium chloride, gallium nitrate, gallium sulfate and gallium bromide.

20. A radiopharmaceutical composition according to claim 1, wherein said composition includes a complex of radioactive gallium and transferrin.

21. A radiopharmaceutical composition according to claim 1, wherein said composition includes an organic salt of non-radioactive indium selected from the group consisting of indium citrate, indium lactate, indium tartrate, indium phytate and indium phthallate.

22. A radiopharmaceutical composition according to claim 1, wherein said composition includes an inorganic salt of non-radioactive indium selected from the group consisting of indium chloride, indium nitrate, indium sulfate and indium bromide.

23. A radiopharmaceutical composition according to claim 1, wherein said composition includes a non-radioactive indium-transferrin complex.

24. A radiopharmaceutical composition, consisting essentially of:
an effective tumor imaging amount of radioactive gallium, an effective tumor imaging improving amount of non-radioactive indium; and
a pharmaceutically acceptable carrier or diluent.

* * * * *